(12) United States Patent
Shah et al.

(10) Patent No.: US 8,541,372 B2
(45) Date of Patent: Sep. 24, 2013

(54) ISOLATED EXTRACELLULAR MATRIX MATERIAL INCLUDING SUBSEROUS FASCIA

(75) Inventors: Bhavin Shah, West Lafayette, IN (US); Katie L. Harrigan, Cordova, TN (US)

(73) Assignee: Cook Biotech Incorporated, West Lafayette, IN (US)

( * ) Notice: Subject to any disclaimer, the term of this patent is extended or adjusted under 35 U.S.C. 154(b) by 0 days.

(21) Appl. No.: 12/983,350

(22) Filed: Jan. 3, 2011

(65) Prior Publication Data

US 2011/0152196 A1  Jun. 23, 2011

Related U.S. Application Data

(63) Continuation of application No. PCT/US2009/049079, filed on Jun. 29, 2009.

(60) Provisional application No. 61/077,423, filed on Jul. 1, 2008.

(51) Int. Cl.
*A61K 38/39* (2006.01)
*A61K 47/48* (2006.01)
*A61K 38/00* (2006.01)

(52) U.S. Cl.
USPC .......................................... 514/17.2; 514/1.1

(58) Field of Classification Search
None
See application file for complete search history.

(56) References Cited

U.S. PATENT DOCUMENTS

| | | | |
|---|---|---|---|
| 2,127,903 A | 3/1938 | Bowen | |
| 2,167,251 A | 7/1939 | Rogers | |
| 3,272,204 A | 9/1966 | Artandi et al. | |
| 4,321,914 A | 3/1982 | Begovac et al. | |
| 4,361,552 A | 11/1982 | Baur, Jr. | |
| 4,755,593 A * | 7/1988 | Lauren | 530/356 |
| 4,781,176 A | 11/1988 | Ravo | |
| 4,801,299 A | 1/1989 | Brendel et al. | |
| 4,902,508 A | 2/1990 | Badylak et al. | |
| 4,956,178 A | 9/1990 | Badylak et al. | |
| 4,969,902 A | 11/1990 | Ravo | |
| 5,269,774 A | 12/1993 | Gray | |
| 5,281,422 A | 1/1994 | Badylak et al. | |
| 5,554,389 A | 9/1996 | Badylak et al. | |
| 5,955,110 A | 9/1999 | Patel et al. | |
| 6,099,567 A | 8/2000 | Badylak et al. | |
| 6,206,931 B1 | 3/2001 | Cook et al. | |
| 6,379,710 B1 | 4/2002 | Badylak et al. | |
| 6,475,232 B1 | 11/2002 | Babbs et al. | |
| 6,576,618 B1 | 6/2003 | Herndon et al. | |
| 2002/0128711 A1 * | 9/2002 | Tanagho et al. | 623/14.13 |
| 2005/0220848 A1 * | 10/2005 | Bates | 424/443 |

FOREIGN PATENT DOCUMENTS

| | | |
|---|---|---|
| WO | WO 03/002165 A1 | 1/2003 |
| WO | WO 03/084410 * | 10/2003 |
| WO | WO 2008/067085 A2 | 6/2008 |

OTHER PUBLICATIONS

Tal et al, Root coverage of advanced gingival recession: A comparative study between acellular dermal matrix allograft and subepithelial connective tissue grafts, Journal of Periodontology, 2002, vol. 73, No. 12, pp. 1405-1411.*

Heeschen C., et al., "Nicotine stimulates angiogenesis and promotes tumor growth and atherosclerosis," Nature Medicine 7 (2001), No. 7, 833-839.

Johnson C., et al., "Matrix Metalloproteinase-9 is Required for Adequate Angiogenic Revascularization of Ischemic Tissues: Potential Role in Capillary Branching," Circulation Research 94 (2004), No. 2, pp. 262-268.

* cited by examiner

*Primary Examiner* — Cecilia J Tsang
*Assistant Examiner* — Sergio Coffa
(74) *Attorney, Agent, or Firm* — Woodard, Emhardt, Moriarty, McNett & Henry LLP

(57) ABSTRACT

Described are purified extracellular matrix materials isolated from the abdominal wall of animals and including the subserous fascia layer of the abdominal wall. Such medical materials can find use in treating damaged tissue and in certain aspects in providing tissue support for the repair of hernias. Related methods of manufacture and use are also described.

25 Claims, 1 Drawing Sheet

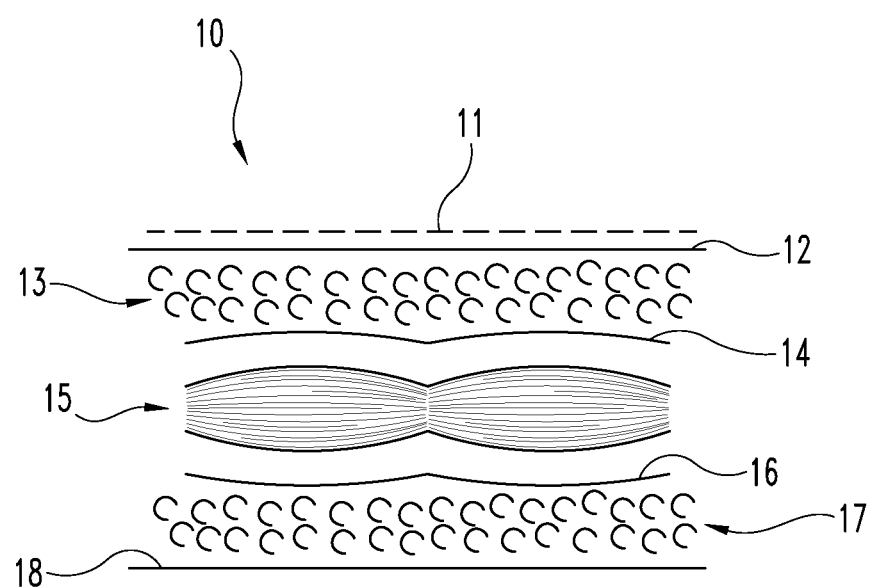

ISOLATED EXTRACELLULAR MATRIX MATERIAL INCLUDING SUBSEROUS FASCIA

REFERENCE TO RELATED APPLICATIONS

This application is a continuation of International Application No. PCT/US2009/049079, filed Jun. 29, 2009, which claims the benefit of U.S. Provisional Patent Application No. 61/077,423, filed Jul. 1, 2008, each of which is hereby incorporated by reference.

BACKGROUND

The present invention resides generally in the field of medical materials and in particular aspects to medical materials useful for tissue grafting.

As further background, a variety of extracellular matrix (ECM) materials have been proposed for use in medical grafting, cell culture, and other related applications. For instance, medical grafts and cell culture materials containing submucosa derived from small intestine, stomach or urinary bladder tissues, have been proposed. See, e.g., U.S. Pat. Nos. 4,902, 508, 4,956,178, 5,281,422, 5,554,389, 6,099,567 and 6,206, 931. In addition, Cook Biotech Incorporated, West Lafayette, Ind., currently manufactures a variety of medical materials based upon small intestinal submucosa under the trademarks SURGISIS®, STRATASIS® and OASIS®.

Medical materials derived from liver basement membrane have also been proposed, for example in U.S. Pat. No. 6,379, 710. As well, ECM materials derived from amnion (see e.g. U.S. Pat. Nos. 4,361,552 and 6,576,618) and from renal capsule membrane (see International PCT Patent Application No. WO 03/002165 published Jan. 9, 2003) have been proposed for medical and/or cell culture applications. Many of these materials, however, are limited by their size and strength. In certain applications, multiple strips or sheets of these materials must be coupled or otherwise bonded together in order to achieve a graft large enough to cover a desired area while still retaining enough strength to prevent the need for re-implantation.

With respect to the above, it is apparent that a need remains for alternate medical materials that can be used in a wide variety of medical applications, particularly those requiring larger-sized and/or relatively extensible grafts. The present invention provides such medical materials, as well as methods of preparing and using the same.

SUMMARY

In one aspect, the present invention provides a material suitable for use in providing a tissue graft. The material comprises an isolated sheet of extracellular matrix material obtained from the abdominal wall of an animal, especially a porcine animal, and including subserous fascia from the abdominal wall of the animal. The extracellular matrix material comprises collagen and elastin, and can be rendered substantially devoid of native cells. The extracellular matrix material is desirably bioresorbable, and can in certain embodiments retain native sulfated glycosaminoglycans from the animal. The extracellular matrix material can have a tensile strength at break of at least one pound and/or an elongation at break of at least about 50%.

In another aspect, the present invention provides a method for preparing an extracellular matrix graft material, the method including providing a segment of tissue isolated from the abdominal wall of an animal, especially a porcine animal, the segment of tissue including subserous fascia and attached subserous fat. At least some of the subserous fat is removed, e.g. mechanically, to produce a collagenous layer of tissue including the subserous fascia. The collagenous layer is decellularized and can also be treated to reduce its content of lipids. In certain beneficial forms, after processing, the collagenous layer of tissue retains native sulfated glycosaminoglycans, has a tensile strength at break of at least one pound, and/or has an elongation at break of at least about 50%.

In another aspect, the present invention provides a method for treating a patient. The method includes grafting a patient with an extracellular matrix material as described herein. In preferred forms, the grafting is conducted so as to provide support to soft tissues of the patient, for example in the conduct of a hernia repair procedure.

Additional embodiments as well as features and advantages of the invention will be apparent from the further descriptions herein.

BRIEF DESCRIPTION OF THE DRAWINGS

FIG. 1 illustrates the layers of a porcine abdominal wall for use in harvesting sections therefrom in order to prepare a graft material.

DETAILED DESCRIPTION

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated medical materials, and further applications of the principles of the invention as illustrated therein are herein contemplated as would normally occur to one skilled in the art to which the invention relates.

As disclosed above, the present invention provides isolated, decellularized extracellular matrix (ECM) materials that can be used in the provision of tissue grafts for medical procedures. Turning now to the drawing, shown in FIG. 1 is a diagram of the layers of the abdominal wall 10 of a pig. FIG. 1 is also representative of the abdominal wall of other animals from which the ECM materials can be obtained, including for example bovine, ovine, and equine animals. The layers include the parietal peritoneum 11, the subserous fascia 12, subserous fat 13, the posterior fascia 14, abdominal muscle 15, the anterior fascia 16, subcutaneous fat 17, and the dermis 18. Extracellular matrix graft materials as described herein include the subserous fascia 12, and optionally also the parietal peritoneum 11, delaminated from the remaining structural layers of the abdominal wall. Thus, preferred extracellular matrix graft materials of the invention and are devoid or essentially devoid of the posterior fascia 14, the abdominal muscle 15, the anterior fascia 16, the subcutaneous fat 17, and the dermis 18. As used herein, "essentially devoid" means that the excluded components are not present except as might be detected as trace remnants, for example making up no more than 0.5% by weight of the graft material.

The subserous fascia of the graft material is derived from the abdominal wall of an animal, preferably a warm-blooded vertebrate, and more preferably a non-human warm-blooded vertebrate such as a porcine, ovine, bovine or equine animal. Porcine animal sources are particularly preferred. In one preferred embodiment, peritoneum and fascia useful in the present invention can be obtained by harvesting the abdominal wall and delaminating a tissue section from the wall including the parietal peritoneum, subserous fascia, and at least portions of other tissue (e.g., adipose tissue) from adjacent tissues including muscle layers and/or other layers occurring in the tissue source. The tissue section including the parietal peritoneum and the subserous fascia is then desirably further processed to prepare a collagen-containing ("collagenous") and elastin-containing ("elastinous") sheet suitable for use as a graft material. The further processing can be conducted in a fashion that removes the parietal peritoneum or that retains the parietal peritoneum. Thus, in certain embodiments, the prepared graft material is devoid or essentially devoid of the parietal peritoneum, and in certain other embodiments, the prepared graft material includes the parietal peritoneum.

A harvested tissue section including at least portions of each of the parietal peritoneum 11, the subserous fascia 12 and subserous fat 13 can be processed to remove the subserous fat 13 using any suitable means. Suitable removal means can include, for example, mechanically abrading the fat tissue, for example with a blunt blade. If desired, additional subserous fat 13 or any other adipose tissue can be removed by soaking the multi-layered material in isopropyl alcohol, or any other liquid medium suitable for removing adipose tissue, for a period of time as necessary to remove additional fat. In one preferred embodiment, the isolated material is first scraped to remove portions of subserous fat 13. After scraping, the material is treated with an organic solvent to remove lipids, for example by soaking in isopropyl alcohol (IPA) (1 part by weight material to 10 parts by volume IPA) for 30 minutes. This treating step for removal of lipids is typically carried out at least once but can be performed multiple times (e.g., 2, 3, 4 or even 5 or more times). Preferred processed ECM graft materials of the invention have a native lipid content of less than 15% by weight, more preferably less than 10% by weight, and in certain embodiments less than 5% by weight.

One advantage of the extracellular matrix materials as described herein is that they can be prepared in larger sizes from a single harvested piece of abdominal wall tissue while still retaining sufficient strength properties for medical purposes. Many other materials isolated from a tissue source (e.g., other ECM materials) require the joining of multiple sheets of material in order to prepare a sheet graft that is larger than any of the individual sheets, thus resulting in an overall sheet of sufficient size and strength for certain medical uses, such as hernia grafts. Extracellular matrix graft materials as described herein can be harvested from animals sufficiently mature and large so as to avoid the need for using multiple, laterally-joined pieces, although such joined constructs can be formed if desired. In certain embodiments, a processed extracellular matrix graft including subserous fascia alone or adjoined to the parietal peritoneum has a width of at least 20 cm and a length of at least 20 cm.

Extracellular matrix materials of the invention can be used to treat a variety of medical conditions, including those involving tissue damage to a patient, by grafting a patient with the materials. In this respect, a medical material of the invention can be used to treat the damaged tissue and can either be applied to an external structure of a patient (e.g., skin) or can be implanted within a patient, for example to provide tissue support as in the case of hernia repair or pelvic floor reconstruction. Accordingly, a medical material of the invention can be configured in a variety of forms to suit its desired site of use. Medical materials of the invention can incorporate one or more drugs or other pharmaceutical agents and can elute those substances after application to the patient, thereby eliminating or diminishing the need for systemic administration of the substance and minimizing the risk of systemic toxicity and adverse reactions.

Generally, when configured for application to tissue, the medical material is cut or otherwise configured to a desired size for its end use. In certain embodiments, the material can be sized larger than the tissue defect to which it is applied. Sizing the material in this way allows for easy attachment to the surrounding tissue. For example, once the sized medical material has been placed on, in, or around the area in need of treatment, the medical material can be more securely attached to the surrounding tissue or other structure using any of several known suitable attachment means. Suitable attachment means include, for example, stapling, suturing, bonding and the like. Preferably, the medical material is more securely attached to the surrounding tissue or other structure by sutures. There are a variety of synthetic materials currently available in the art for use as sutures. For example, sutures comprising Prolene™, Vicryl™, Mersilene™ Panacryl™, and Monocryl™, are contemplated for use in the invention. Other suture materials will be well known to those skilled in the art. Medical adhesives as generally known in the art can also be used in conjunction with the medical materials of the invention to more securely attach the material to tissue or other structure.

In preferred embodiments, the extracellular matrix material including peritoneum and subjacent subserous fascia can be a bioresorbable material, desireably supporting tissue remodeling when implanted in a patient so as to be replaced by patient tissue over time. In many cases, the medical material will exhibit remodelable properties such that the remodeling process occurs over the course of several days or several weeks. In preferred embodiments, the remodeling process occurs within a matter of about 5 days to about 12 weeks, during which the implanted material is resorbed and replaced by tissue of the patient. In so doing, preferred ECM materials of the invention can support or induce angiogenesis into the material, to facilitate the development of new patient tissue. For these purposes, certain preferred ECM materials of the invention are not treated with a chemical crosslinking agent such as glutaraldehyde, so as to avoid making the materials permanent upon implantation.

If desired for a given situation, though, in other embodiments the inventive ECM material can contain introduced, non-native crosslinks. For example, the ECM material can be treated with a crosslinking agent at any point after it is isolated from its source. Increasing the amount (or number) of crosslinkages within the medical material and/or between two or more laminated layers of the medical material can be used to enhance its strength. However, introduced crosslinkages within the medical material may also affect its ability to become resorbed and to remodel into patient tissue. Consequently, in certain embodiments in which crosslinking is introduced, the level of added crosslinking within the ECM material can be judiciously controlled to preserve a remodelable character of the ECM material.

When used, introduced crosslinking of the ECM material may be achieved by photo-crosslinking techniques, or by the application of a crosslinking agent, such as by chemical crosslinkers, or by protein crosslinking induced by dehydration or other means. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

When laminate construct containing two or more layers of the ECM material is contemplated, the layers of the laminate can be additionally crosslinked to bond multiple layers of the ECM material to one another. Cross-linking of the ECM materials can also be catalyzed by exposing the matrix to UV radiation, by treating the collagen-based matrix with enzymes such as transglutaminase and lysyl oxidase, and by photocross-linking. Thus, additional crosslinking may be added to individual layers prior to coupling to one another, during coupling to one another, and/or after coupling to one another.

Alternatively, two or more multi-layered medical material segments can be rolled or stacked, or one material segment folded over itself at least one time, and then the materials can be fused or bonded together using a bonding technique other than chemical cross-linking, such as vacuum pressing, lyophilization, or other dehydrothermal bonding conditions and/or the use of an adhesive, glue or other bonding agent. Suitable bonding agents may include, for example, collagen gels or pastes, gelatin, fibrin glues, or other agents including reactive monomers or polymers, for example cyanoacrylate adhesives. As well, bonding can be achieved or facilitated using chemical cross-linking agents, such as glutaraldehyde, formaldehyde, epoxides, genipin or derivatives thereof, carbodiimide compounds, polyepoxide compounds, or other similar agents, including those others identified in the discussions above. The combination of one or more of these with dehydration-induced bonding may also be used.

A variety of dehydration-induced bonding methods can be used to fuse portions of the inventive ECM materials together. In one preferred embodiment, multiple layers of the ECM material are compressed under dehydrating conditions. The term "dehydrating conditions" can include any mechanical or environmental condition which promotes or induces the removal of water from the multi-layered medical material. To promote dehydration of the compressed material, at least one of the two surfaces compressing the matrix structure can be water permeable. Dehydration of the material can optionally be further enhanced by applying blotting material, heating the matrix structure or blowing air, or other inert gas, across the exterior of the compressing surfaces. Particularly useful methods of dehydration bonding the ECM layers to one another include lyophilization, e.g. freeze-drying or evaporative cooling conditions.

Another method of dehydration bonding vacuum pressing. During vacuum pressing, dehydration of the multi-layered medical materials in forced contact with one another effectively bonds the materials to one another, even in the absence of other agents for achieving a bond, although such agents can be used while also taking advantage at least in part of the dehydration-induced bonding. With sufficient compression and dehydration, the multi-layered medical materials can be caused to form a generally unitary laminate structure.

It is advantageous in some aspects of the invention to perform drying operations under relatively mild temperature exposure conditions that minimize potential deleterious effects upon the ECM materials of the invention, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

As prepared, the ECM material may optionally retain bioactive components native to the source tissue. For example, the peritoneum and/or fascia may include one or more native growth factors, such as Fibroblast Growth Factor-2 (FGF-2), Vascular Endothelial Growth Factor (VEGF), or a combination thereof. As well, the inventive ECM material may include other biological materials such as one or more sulfated glycosaminoglycans (sGAGs) such as heparin sulfate, one or more non-sulfated glycosaminoglycans such as hyaluronic acid, and/or one or more glycoproteins such as fibronectin. Thus, generally speaking, the inventive ECM may optionally be processed so as to retain one or more native bioactive components that induces, directly or indirectly, a cellular response such as a change in cell morphology, proliferation, growth, protein or gene expression.

The processed ECM materials of the invention will typically include abundant collagen. Such naturally-derived ECM materials will for the most part include collagen fibers that are non-randomly oriented. The processed ECM materials will also typically include elastin. When processed to retain native bioactive components as discussed above, the ECM material can retain these components as solids interspersed between, upon and/or within the collagen fibers. Particularly desirable materials for use in the invention will include significant amounts of such interspersed, non-collagenous and non-elastinous solids that are readily ascertainable under light microscopic examination with appropriate staining. Such non-collagenous and non-elastinous solids can constitute a significant percentage of the dry weight of the material in certain inventive embodiments, for example at least about 1%, at least about 3%, and at least about 5% by weight in various embodiments of the invention.

The ECM material of the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels. Methods for measuring in vivo angiogenesis in response to biomaterial implantation have recently been developed. For example, one such method uses a subcutaneous implant model to determine the angiogenic character of a material. See, C. Heeschen et al., *Nature Medicine* 7 (2001), No. 7, 833-839. When combined with a fluorescence microangiography technique, this model can provide both quantitative and qualitative measures of angiogenesis into biomaterials. C. Johnson et al., *Circulation Research* 94 (2004), No. 2, 262-268.

Further, in addition or as an alternative to the inclusion of native bioactive components, non-native bioactive components such as those synthetically produced by recombinant technology or other methods, may be incorporated into ECM materials of the invention. These non-native bioactive components may be naturally-derived or recombinantly produced proteins that correspond to those natively occurring in the tissue, but perhaps of a different species (e.g. human proteins applied to tissue from other animals, such as pigs). In certain forms, one or more non-native growth factors such as FGF-2, platelet derived growth factor (PDGF) and/or VEGF, can be added to the ECM material. The non-native bioactive components may also be drug substances. Illustrative drug substances that may be incorporated into and/or onto the materials used in the invention include, for example, antibiotics, thrombus-promoting substances such as blood clotting factors, e.g. thrombin, fibrinogen, anti-inflammatory agents, anti-proliferative agents, analgesic agents, and others. These substances may be applied to the multi-layered medical material as a premanufactured step, immediately prior to the procedure (e.g. by soaking the material in a solution containing a suitable antibiotic such as cefazolin), or during or after engraftment of the material in the patient.

A non-native bioactive component can be applied to the inventive ECM material by any suitable means. Suitable means can include, for example, spraying, impregnating, dipping, etc. If other chemical or biological components are included in the ECM material, the non-native bioactive component can be applied either before, in conjunction with, or after these other components. In one embodiment, a coating of a non-native bioactive component can be formed on either or both sides of the ECM material. By "coating" is meant that the non-native bioactive component is applied so as to cover a designated portion of a surface of the ECM material. In certain embodiments, a non-native bioactive component can be applied to form a coating which substantially covers the entire surface area of at least one side of an inventive ECM material. In other embodiments, a non-native bioactive component such as those discussed herein can be incorporated substantially homogenously throughout the inventive ECM material.

The ECM material of the invention is preferably highly purified, for example, as described in U.S. Pat. No. 6,206,931 to Cook et al. Thus, preferred ECM materials will exhibit an endotoxin level of less than about 12 endotoxin units (EU) per gram, more preferably less than about 5 EU per gram, and most preferably less than about 1 EU per gram. As additional preferences, the inventive ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 $\mu$g/mg, more preferably less than about 2 $\mu$g/mg, and virus levels are preferably less than about 50 plaque forming units (PFU) per gram, more preferably less than about 5 PFU per gram. These and additional properties of ECM tissue as taught in U.S. Pat. No. 6,206,931 may be characteristic of the inventive ECM material.

In additional embodiments, the ECM material of the invention can be subjected to processes that expand the material. In certain forms, such expanded material can be formed by the contacting the ECM material with one or more alkaline substances until the material expands. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner. Illustratively, the expanded material can be enriched with bioactive components, dried, and/or molded, etc., in the formation of a graft construct of a desired shape or configuration. In certain embodiments, an expanded ECM material construct can be highly compressible and expandable such that the material can be compressed for delivery, such as from within the lumen of a cannulated delivery device, and thereafter expand upon deployment from the device so as to become anchored within a patient, cause closure of a tract within the patient, and/or cause hemostasis.

Expanded materials can be formed by the controlled contact of the inventive ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

The ECM material will typically include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the ECM material can be in the range of about 0.5 to about 2 M, with a concentration of about 1 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the ECM material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the ECM material is exposed to a 1 M solution of NaOH having a pH of 14 at a temperature of about 37° C. for about 1.5 to 2 hours. Such treatment results in collagen denaturation and a substantial expansion of the material. Denaturation of the collagen matrix of the material can be observed as a change in the collagen packing characteristics of the material, for example a substantial disruption of a tightly bound collagenous network of the starting material. A non-expanded material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded ECM material typically appears more porous than a corresponding non-expanded ECM material. Moreover, in many instances, the expanded ECM material can be demonstrated as having increased porosity, e.g. by measuring for an increased permeability to water or other fluid passage as compared to the non-treated starting material. The more foamy and porous structure of an expanded ECM material can allow the material to be cast or otherwise prepared into a variety of sponge or foam shapes for use in the preparation of medical materials and devices.

After such alkaline treatments, the ECM material can be isolated from the alkaline medium and processed for further use. Illustratively, the collected material can be neutralized and/or rinsed with water to remove the alkalinity from the material, prior to further processing of the ECM material to form constructs or other compositions of the invention.

A starting material (i.e., prior to treatment with the alkaline substance) can optionally include native components other than collagen and elastin. Treating the material with an alkaline substance may reduce the quantity of one, some or all of such native components. In certain embodiments, controlled treatment of the material with an alkaline substance will be sufficient to create a material which is substantially devoid of nucleic acids and lipids, and potentially also of growth factors, glycoproteins, glycosaminoglycans, and proteoglycans.

In certain embodiments, one or more bioactive components, exogenous or endogenous, for example, similar to those removed from the ECM material during expansion processing, can be returned to the material. For example, the expanded ECM material can be replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989, containing these components can be prepared and applied to an ECM material from which they were removed. In one embodiment, the ECM material can be incubated in a tissue extract for a sufficient time to allow bioactive components contained therein to associate with the material. The tissue extract may, for example, be obtained from non-expanded ECM tissue of the same type used to prepare the expanded ECM material that is being replenished. Other means for returning or introducing bioactive components to multi-layered medical material include spraying, impregnating, dipping, etc. as known in the art.

An ECM material as described herein can be used to manufacture compositions or devices of any suitable form. Suitable forms include, for example, sheets, porous solid foams, powders, plugs, tubes, solid cylinders, suspensions in liquid media, gels, or solutions including solvated ECM components.

The thickness of a single isolated, decellularized ECM layer of the invention will vary with the animal from which it is isolated, including variations based on species, the age or size of the animal, and the like. Preferred such single layers have a thickness (hydrated) in the range of about 500 to about 1000 microns, more preferably about 600 to 900 microns, and most preferably about 750 to about 850 microns. The single ECM layer will desirably have a tensile strength at break when hydrated of at least about one pound, and in certain forms in the range of about one to five pounds. The single ECM layer will desirably be highly extensible, having an elongation at break when hydrated of at least about 50%, and typically in the range of about 50% to about 80%. In this regard, the tensile strength at break and elongation at break as referred to herein can be determined in accordance with ASTM D882 (2002) or an equivalent method. The single ECM layer will desirably exhibit a suture retention strength when hydrated in the range of about 0.5 to about 2 pounds based upon a 5-0 Prolene suture size and a bite depth of 2 mm. Similarly, the single ECM layer will desirably exhibit a burst strength when hydrated in the range of about 200 to about 1000 kPa. Porcine-derived ECM layers of the invention having such thicknesses, tensile strengths at break, elongations at break, suture retention strengths, and/or burst strengths are particularly preferred.

If needed to achieve enhanced mechanical or other physical properties, multiple layers of the ECM material can be bonded together in any suitable fashion, including dehydrothermal bonding under heated, non-heated or lyophilization conditions, using adhesives as described herein, glues or other bonding agents, crosslinking with chemical agents or radiation (including UV radiation), or any combination of these with each other or other suitable methods as described above. For example, constructs having two, three, four, five, six, or more of the ECM layers bonded to one another can be prepared. In such constructs, the ECM layers can be directly superimposed upon one another to completely overlap, or can be arranged to only partially overlap and thereby create an overall sheet that has a larger surface area than any of the ECM layers considered individually. Combinations of completely and only partially overlapped ECM layers can also be used in forming constructs of the invention. One advantage of the peritoneum/subserous fascia ECM layers of the invention is that they can be isolated in relatively large surface area sizes, thus eliminating or reducing the need for partial overlapping of separate ECM layers to achieve a relatively large sheet construct. Consistently, in certain preferred embodiments of the invention, a multilaminate sheet construct includes at least two of the peritoneum/subserous fascia ECM layers bonded to one another and forming an overlapped region, wherein the overlapped region has a surface area of at least 400 $cm^2$. In such constructs, the at least two ECM layers can be completely overalapped to provide a construct with a surface area of 400 $cm^2$ or more, or only partially overlapped but with sufficient overlapped material to form an overlapped surface area of at least 400 $cm^2$. In each case, the 400 $cm^2$ overlapped region may include a length of at least 20 cm and a width (measured perpendicular to the length) of at least 20 cm. Such constructs can provide ECM sheet devices with a large strengthened and stable region of material, for example for use in providing soft tissue support such as in hernia repair or pelvic floor reconstruction.

Sterile medical products produced with ECM materials as described herein can be devoid of synthetic materials, such as synthetic polymeric materials, or can include the ECM materials combined with one or more synthetic (e.g. synthetic polymeric) materials, for example in a multi-layered laminate structure. For example, a multi-layered medical material can include synthetically produced layers be attached to the extracellular matrix tissue, for example by sutures, adhesives, or the like. Such synthetically produced materials can include non-bioresorbable or bioresorbable synthetic polymer materials such as polytetrofluroethylene (PTFE, e.g. GORE-TEX material), nylon, polypropylene, polyurethane, silicone, DACRON polymer, polyglycolic acid (PGA), polylactic acid (PLA), copolymers of glycolic acid and lactic acid (PLGA copolymers), polycaprolactone, or others as generally known in the art.

Medical products including ECM materials of the invention can be provided in sterile form in medical packaging. Terminal sterilization of the packaged product may be achieved, for example, by irradiation, ethylene oxide gas, or any other suitable sterilization technique, and the materials and other properties of the medical packaging can be selected accordingly.

ECM materials of the invention can be packaged in a dehydrated or hydrated state. Dehydration of the ECM material can be achieved by any means known in the art, including any of those discussed hereinabove. Preferably, the packaged ECM material is a lyophilized or vacuum pressed material. If desired, a suitable liquid, such as sterile water or a sterile aqueous buffer, can be used to rehydrate a dehydrated ECM material prior to use to treat a patient. Alternatively, the ECM material can be applied to the patient in its dehydrated form.

For the purpose of promoting a further understanding of aspects of the present invention and their features and advantages, the following specific Examples are provided. It will be understood that these Examples are illustrative, and not limiting, of aspects of the present invention.

EXAMPLE 1

Preparation of Extracellular Matrix Graft Material

At a packing plant, a tissue section was harvested at the point on the processing line where the complete porcine body cavity had been opened with a midline incision and the anterior ribs and all organs had been removed. An incision was made on the posterior edge of the body wall flap on each side of the body, and a tissue section was pealed off of each side of the body wall so as to produce two tissue sections of approximately equal size (1 ft×1.5 ft). These sections included the peritoneum, the subserous fascia and subserous fat. It was confirmed that the posterior fascia was not part of this tissue section. The subserous fat was about 0.5 to about 1 cm thick depending on location along the section. The peritoneum was located, which included both the visceral peritoneum and the parietal peritoneum. The visceral peritoneum, which was identified as a thin, transparent film laced with a white, thick network of blood vessels, was discarded.

To remove fat, the tissue sections were scraped on both sides by hand with a Teflon sheet (⅛" thick). The tissue sections were observed to be tear resistant during this operation. Each tissue section was weighed to be approximately 143 g after scraping.

Once weighed, each tissue section was disinfected in a solution containing 100 mL ethanol (200 proof), 12 mL peracetic acid (PAA), and 1990 mL high purity water. The sections were shaken in this solution for approximately 2 hours and subsequently rinsed five times for five minutes each in high purity water. The sections were then stored under high purity water. Observations suggested that the sections had been rendered devoid or essentially devoid of the parietal peritoneum during the described processing.

The resulting tissue sections as described above were applied on pinned delrin panels and freeze-dried. This resulted in white, thick lyophilized sheets with a distinct smooth side and rough side. These sheets were rinsed twice in pure isopropyl alcohol (IPA) (1 part by weight sheet to 10 parts by weight IPA) for 30 minutes each rinse, to remove lipids. After IPA treatment, the sheets were rinsed twice for five minutes each in high purity water. The sheets were then stored under high purity water. A piece of hydrated sheet was tested for thickness and probe burst. The thickness values were 0.734 mm, 0.755 mm, 0.811 mm, 0.804 mm, 0.796 mm, and 0.818 mm with an average thickness of 0.786 mm and standard deviation of 0.034 mm. The probe burst force observed was 125 N, 89.2 N, and 98 N with an average of 104.1 N and a standard deviation of 18.6 N.

EXAMPLE 2

Testing for Native Lipid Content

Two lots of material were obtained generally as described in Example 1. The abdominal wall tissue sections were processed by mechanical scraping, chemical defatting with three treatments with 100% isopropyl alcohol (IPA) (1:10 wt:vol), disinfection with peracetic acid (PAA) solution, and four washes with high purity water. Each lot was made up of two sheets for a total of four sheets that were tested. Four 4×7 cm samples were cut from each sheet resulting in 8 samples per lot and 16 samples in total. Each sample was weighed (initial weight), rolled and placed in a 1.5 mL centrifuge tube with 10 mL of 100% ethanol. The tubes were placed into a tube holder and the holder was placed on its side on a rotating shaker for approximately 24 hours at room temperature. After 24 hours, the ethanol was drained and 10 mL of 100% acetone was placed in each tube. The holder was then placed back onto the shaker for approximately 24 hours at room temperature. After 24 hours, the acetone was drained and the samples were allowed to air dry for approximately 24 hours in a fume hood. Samples were subsequently dried for approximately 48 hours and weighed (final weight). Lipid content was calculated by the initial weight minus the final weight divided by the initial weight.

The mean measured lipid content in the material was determined to be 8.4%±6.4%.

EXAMPLE 3

Testing for Native Hyaluronic Acid Content

Two lots of material were obtained generally as described in Example 1. The abdominal wall tissue sections were processed by mechanical scraping, chemical defatting with three treatments of 100% isopropyl alcohol (IPA) (1:10 wt:vol), disinfection with peracetic acid (PAA) solution, and four washes with high purity water. Each lot was made up of two sheets for a total of four sheets that were tested. Four 12 mm disc samples were cut from each sheet resulting in 8 samples per lot and 16 samples in total. Each sample was weighed (initial weight), rolled and placed in 1.5 mL centrifuge tubes with 450 µl of sterile phosphate buffered saline (PBS) and 50 µl of proteinase K at 56° C. for 45 minutes. Samples were then pulverized with tissue grinders for 90 seconds per sample. Tubes with samples were centrifuged at 12000 g for 5 minutes at 4° C. to pellet any undigested material. A 1:40 dilution of the supernatant was made by adding 10 µl of digested sample to 390 µl PBS, followed by vortexing. Hyaluronic acid content was measured by Corgenix HA ELISA kits per manufacture's instructions. Hyaluronic acid weight content was calculated by dividing the sample hyaluronic acid content by the initial weight of the sample.

The mean measured hyaluronic acid content in the material was determined to be 13±24.5 µg/g.

EXAMPLE 4

Testing for Native Sulfated Glycosaminoglycan (sGAG) Content

Two lots of material obtained generally as described in Example 1. The abdominal wall tissue sections were processed by mechanical scraping, chemical defatting with three treatments of 100% isopropyl alcohol (IPA) (1:10 wt:vol), disinfection with peracetic acid (PAA) solution, and four washes with high purity water. Each lot was made up of two sheets for a total of four sheets that were tested. Eight 12 mm disc samples were cut from each sheet resulting in 16 samples per lot and 32 samples in total. Each sample was weighed (initial weight), rolled and placed into 1.5 mL centrifuge tubes with 450 µl of sterile PBS and 50 µl of proteinase K at 56° C. for 45 minutes. Samples were then pulverized with tissue grinders for 90 seconds per sample. Tubes with samples were then centrifuged at 15000 rpm for 10 minutes to pellet any undigested material.

16 of the 32 samples were assayed for sGAG content using the Blyscan sGAG assay. Each test sample consisted of 90 µl high purity water and 10 µl of the sample digest. All tubes were vortexed for 5 seconds and then 1.0 mL of Blyscan dye reagent was added. The tubes were incubated for 30 minutes at room temperature and were vortexed 4 times for 5 seconds per sample. Each sample was then spun at 15000 rpm for 10 minutes, and the resulting supernatant was removed. Each pellet was resuspended in 1.0 mL of dissociation reagent from they Blyscan Assay kit. All samples were incubated one hour at 37° C. with agitation and were vortexed 3 times for 5 seconds vortexing per tube. 100 µl aliquots of the resulting solution were made in triplicate and were pipetted into two wells of a 96-well plate. Absorbance readings at 656 nm were taken. A standard curve was generated for the GAG standards used for the Blyscan sGAG assay.

The remaining 16 samples were assayed for sGAG content using the DMMB method. Individual samples were placed in 1.5 mL eppendorf centrifuge tubes and 180 µl of sterile PBS and 20 µl proteinase K solution were added to each tube. Samples were digested for 15 minutes at 56° C. with intermittent vortexing. A heparin standard curve was made using purified heparin in high purity water at 20 µg/mL, 50 µg/mL and 100 µg/mL.

100 µl aliquots of DMMB samples were made in triplicate and placed in 15 mL centrifuge tubes. Triplicate 100 µl aliquots of blank (high purity water), and heparin standards, were also placed in 15 mL centrifuge tubes. To each tube, 2.5 mL of DMMB solution was added. Solutions were vortexed and 100 µl aliquots of each tube were aliquoted into a well of a 96-well plate. Absorbance readings at 600 nm were taken. A standard curve was generated for the heparin standard concentrations.

sGAG concentration was calculated from the heparin standard curve or the GAG standard curve. The weight content of sGAG was determined by dividing the sGAG content by the weights of the samples. The mean measured sGAG content using the Blyscan assay was 1656 µg/g±3164 µg/g. The mean measured sGAG content using the DMMB method was 1070 µg/g±460 µg/g.

EXAMPLE 5

Testing for Native Visible Nuclei and Native Lipid Content in Materials Processed by Various Methods Four lots of material were obtained generally as described in Example 1. The abdominal wall tissue sections were processed by mechanical scraping to remove the dense adipose tissue layer. Each lot was made up of two sheets for a total of eight sheets that were tested. Each sheet was cut into nine 7×10 cm samples. One sample from each lot was chemically processed in a 0.2 percent by volume peracetic acid in a 5 percent by volume aqueous ethanol solution for a period of two hours with agitation ("the PAA Group"), and one sample from each lot was chemically processed generally as described in Example 13 of International Publication No. WO2008067085 (Cook Biotech Incorporated) dated Jun. 5, 2008, publishing International Application No. PCT/US2007/082238 filed Oct. 23, 2007 ("the '085 Group"). The remaining 28 samples were divided randomly into two groups. The first group was treated in isopropyl alcohol (IPA) and acetone solutions whereas the second group was treated in chloroform and methanol solutions as shown in Table 1, to result in a reduction of the level of native lipids.

TABLE 1

| Step | w/v ratio | Chemical/Solution | Time |
|---|---|---|---|
| IPA/Acetone Groups | | | |
| 1 | 1:10 | IPA | ½ hr |
| 2 | 1:10 | IPA | 1 hr |
| 3 | 1:10 | Acetone | 1 hr |
| 4 | 1:10 | IPA | ½ hr |
| 5 | 1:10 | HPW | 5 min |
| 6 | 1:10 | HPW | 5 min |
| Chloroform/Methanol Groups | | | |
| 1 | 1:10 | Methanol | ½ hr |
| 2 | 1:20 | Chlor/Meth | 1 hr |
| 3 | 1:10 | Methanol | ½ hr |
| 4 | 1:10 | HPW | 5 min |
| 5 | 1:10 | HPW | 5 min |

After this treatment, 2 samples from each alcohol treatment group were subjected to one of seven treatment groups which were designed to strip the fascia of the majority of non-collagen components. The six treatment groups are summarized in Table 2.

TABLE 2

| Step | w/v ratio | Chemical/Solution | Time |
|---|---|---|---|
| Triton Groups | | | |
| 1 | 1:10 | 1% Triton/0.02% EDTA | 24 hrs |
| 2 | 1:10 | HPW | 5 min |
| 3 | 1:10 | HPW | 5 min |
| SDS + TBE Groups | | | |
| 1 | 1:10 | 0.1% SDS | 2 hrs |
| 2 | 1:10 | 1 × TBE | 2 hrs |
| 3 | 1:10 | HPW | 5 min |
| 4 | 1:10 | HPW | 5 min |
| Trypsin Groups | | | |
| 1 | 1:10 | 0.25% Trypsin/0.05% EDTA | 2 hrs |
| 2 | 1:10 | HPW | 5 min |
| 3 | 1:10 | HPW | 5 min |
| 4 | 1:10 | HPW | 5 min |
| 5 | 1:10 | HPW | 5 min |
| 2-Mercaptoethanol Groups | | | |
| 1 | 1:10 | 5 mM 2-Mercaptoethanol | 4 hrs |
| 2 | 1:10 | HPW | 5 min |
| 3 | 1:10 | HPW | 5 min |
| 4 | 1:10 | HPW | 5 min |
| 5 | 1:10 | HPW | 5 min |
| Acid Groups | | | |
| 1 | 1:10 | 1M HCl | 2 hrs |
| 2 | 1:10 | HPW | 5 min |
| 3 | 1:10 | HPW | 5 min |
| Alkaline Groups | | | |
| 1 | 1:10 | 1M NaOH | 2 hrs |
| 2 | 1:10 | HPW | 5 min |
| 3 | 1:10 | HPW | 5 min |

Once all treatments were complete, the samples were placed in 0.2% PAA for 2 hours on an orbital shaker. A 2×2 cm sample of wet tissue was removed for nuclei assessment. The remaining sample was lyophilized and a 2×7 cm sample was cut for lipid analysis. A total of 32 samples were used for each test.

For the lipid analysis, each sample was weighed and the starting weight was recorded. Each sample was then rolled and placed in a 15 mL centrifuge tube with 10 mL 100% ethanol. The tubes were placed into a tube holder and the holder was placed on its side on a rotating shaker for approximately 24 hours at room temperature. After 24 hours, the ethanol was drained and 10 mL of 100% acetone was placed in each tube and the holder placed back onto the shaker for approximately 24 hours at room temperature. After the 24 hours, the acetone was then drained and the samples were allowed to air dry for approximately 48 hours in a fume hood. At the end of the drying time, each sample was weighed and the end weight was recorded. The amount of lipid extracted was calculated by subtracting the end weight from the starting weight. This amount was then divided by the starting weight to calculate the weight percent lipid the material contained.

The average overall lipid content (in weight percent) for the various groups were: PAA Group—16%; the '085 Group—9%; IPA/Acetone Group—3%; Chloroform/Methanol Group—7%.

For visible nuclei assessment, a solution of Hoechst 33528 stain was made for staining the samples. A total of 250 mL of staining solution was made by diluting a stock solution of 1 mg/mL Hoechst in methanol to 1 μg/mL in phosphate buffered saline (250 μl of Hoechst stock into 250 mL of PBS). Each sample was incubated in 5 mL of Hoechst staining solution for 15 minutes at room temperature with shaking. After staining, each sample was rinsed 3 times with PBS for 5 minutes at room temperature with shaking. Each stained sample was placed onto a glass microscope slide and a 22 mm×22 mm glass coverslip was placed on top of the sample and lightly pressed to remove any air bubbles. The slide was then placed on the microscope stage. The stage was adjusted to put the sample underneath the objective at a random location for the sample. The focus was adjusted to provide an image with the most number of in focus nuclei as possible for that location. The image was then taken using SpotRT software. The image was then adjusted by selecting grayscale and negative to give the nuclear staining as dark dots on a light background. The brightness, contrast and gamma were sometimes adjusted to ensure the easiest determination of nuclei. A single count of the visible nuclei on each image was made after printing the images onto paper. The counts are displayed as number of nuclei per field.

The number of nuclei for a 0.263 mm$^2$ representative field of each sample was counted. The samples which had greater than approximately 300 nuclei in the visible field were deemed too numerous to count as this procedure was being used as a screening tool for the efficacy of a treatment protocol rather than a definitive quantification of nuclei.

Most of the treatments were more effective at removing nuclei after treatment with IPA and acetone. This may suggest that either the IPA/acetone treatment makes cells more susceptible to lysing or the chloroform/methanol treatment makes cells less susceptible to lysing. Overall, the tissues treated with NaOH had the lowest number of remaining nuclei, but was somewhat jelly-like and swollen post treatment. This effect is typical for collagen treated in alkaline solutions and would likely affect the strength of the material due to its effect on the organization of the collagen fibers. Trypsin treated tissue also performed well in terms of nuclei removal, but the tissues were easily torn and difficult to handle due to its liquid-like nature. These characteristics are undesirable for a potential hernia repair material so this treatment was eliminated. The tissue treated with SDS and TBE had very few visible nuclei, and did not seem to suffer any material strength changes.

EXAMPLE 6

Mechanical Characterization of Graft Material

Six lots consisting of two slabs of tissue each of abdominal wall fascia were obtained. The twelve tissue slabs were processed by mechanically removing a dense adipose tissue layer. Six sheets (one from each lot) were placed into 0.2% peracetic acid (PAA) solution for two hours on an orbital shaker. The remaining six sheets were treated in isopropyl alcohol (IPA) and acetone solutions before being divided into two treatment groups. The first group was treated for one hour in 1 M NaOH. The second group was placed into 0.1% SDS at 37° C. for one hour and 1×TBE at 37° C. for one hour. Both groups were rinsed four times in high purity water after treatment completion and disinfected in 0.2% PAA for two hours. After four rinses in high purity water, all tissue samples were stored in high purity water at 4° C. After a minimum of 24 hours in refrigerated storage, all sheets were lyophilized. All treatments and washes were done in a 1:10 weight:volume ratio.

For tensile strength testing, four dog bone-shaped samples were cut from each lyophilized sheet for a total of 48 samples. The samples were 65 mm long with a 5 mm wide central portion and 12 mm wide end portions. The tensile strength at break of each test sample was calculated as the maximum load found in the data file for that test sample. The Instron Table-Top Servohydraulic Testing System (8840 Series) was used. The rate of travel of the power-actuated grip was a uniform 100 mm/minute. The load cell resolution was 0.0025 N. The maximum error recorded in calibration (tension: 1-100 N) was 0.44%. The tensile strength at break of each test sample was calculated as the maximum load for that sample divided by the width and thickness of that test sample. The average tensile force at break of the PAA-treated material samples was 2.32 N. The average tensile force at break of the NaOH-treated material samples was 3.41 N. The average tensile force at break of the SDS-treated material samples was 3.03 N. There was no statistical difference between any of the groups tested which suggests that the treatments have little effect on the tensile strength of the material.

For suture retention strength testing, four articles were cut from each lyophilized sheet for a total of 48 samples. Each test article was a 2 cm in length by 1 cm wide. A steel wire with the same diameter as 5-0 prolene suture was passed through the article at a bite depth of 2 mm. Suture retention strength of the test samples was recorded as the peak load measured on the Instron tensile Test Apparatus during the individual test. All samples tested failed as a result of the stainless steel wire pulling through the material. There was no statistical difference between any of the groups tested which supports the evidence that the treatments have little effect on the structure and strength of the material.

For burst strength testing, four test articles were cut from each lyophilized sheet for a total of 48 samples. The Mullen Burst Tester, Model "CA" was used. Each sample was a 3 in×3 in square. Burst pressure of the test sample was recoded as the tare pressure on the Digiburst display unit for the individual test. Both the burst pressure and tare pressure were recorded for each sample tested. There was no statistical difference between any of the groups tested which further supports the evidence that the treatments have little effect on the structure and strength of the material.

Treating the material with NaOH or SDS/TBE did not have a significant effect on any of the mechanical properties of the material. Overall, the material has an ultimate load of 2.77±0.77 pounds, average suture retention strength of 1.28±0.46 pounds, and an average burst pressure of 520±193 kPa.

EXAMPLE 7

Biochemical Characterization of Graft Material

Six lots (consisting of two tissue slabs each) of abdominal wall fascia were obtained similar to that described in Example 1. Briefly, the twelve tissue slabs were initially processed by mechanically removing a dense adipose tissue layer. Subsequently, six sheets (one from each lot) were placed into 0.2% peracetic acid (PAA) for two hours on an orbital shaker. The remaining six sheets were treated in isopropyl alcohol (IPA) and aceotone solutions before being further divided into two treatment groups. The first group was treated for one hour in 1 M NaOH at room temperature. The second group was placed into 0.1% SDS (37° C.) for one hour then 1×TBE (37° C.) for an additional hour. Both groups were rinsed four times in high purity water after treatment completion and disinfected in 0.2% PAA for two hours. After four rinses in high purity water, all tissue samples were stored in high purity water at 4° C. After a minimum of 24 hours in refrigerated storage, all sheets were lyophilized. All treatments and washes were done in a 1:10 ratio.

For lipid analysis, four test articles were cut from each lyophilized sheet. Each sample measured 2 cm×7 cm. For all other testing, each test group consisted of four 12 mm disks cut from each lyophilized sheet. A total of 288 samples (48 each test, 6 tests) were tested.

For lipid analysis, a total of 48 2 cm×7 cm test samples were evaluated. The amount of lipid extracted was calculated by subtracting the final weight from the initial weight. This amount is then divided by the initial weight to calculate the weight percent lipid the material contained. Lipid content in ECM products has the potential to contribute to inflammatory or immune reactions in vivo by hindering the extraction of cellular components and lipopolysaccharides from the base material. Therefore, it is advantageous to have a means to reduce lipid content in ECM products. Lipid reduction done solely by mechanical scraping resulted in the material having an average lipid content of 19.8%±2.8%. A previous study analyzing the lipid content of similarly treated material showed there to be an average of 8.4%±6.4% (see Example 3). When this material is additionally subjected to a treatment in isopropyl alcohol and acetone, the lipid content is effectively reduced to an average of 2% (see Example 6). Even further lipid reduction potentially occurs by tertiary treatment in 1 M NaOH, which resulted in tissues having an average lipid content of 0.6%, which when lot-matched comparisons are made it is representative of a 95% lipid reduction.

For FGF-2 content, a total of 48 12 mm disk test samples were evaluated. Samples were weighed and weights recorded. Individual samples were placed in 1.5 mL eppendorf centrifuge tubes and 500 µl of sterile 10×PBS was added to teach tube. Samples were pulverized with tissue grinders for 90 seconds per sample. Content of FGF-2 per gram was calculated as described in Example 2. FGF-2 was found to be completely eliminated from the base material with NaOH. SDS and TBE treatments did not have an effect on the FGF-2 content of the material.

For sGAG content testing, a total of 48 12 mm disk test samples were evaluated. Each sample was weighed and the starting weights recorded. Individual samples were placed in 1.5 mL eppendorf centrifuge tubes and 450 µl of sterile 1×PBS and 50 µl of proteinase K solution were added to each tube. Samples were digested for 45 minutes at 56° C., then centrifuged at 15000 rpm for 10 minutes to pellet any undigested material. Each test sample consisted of 80 µl high purity water and 20 µl of the sample digest placed into 1.5 mL centrifuge tube. All tubes were vortexed for 5 seconds and then 1.0 mL of Blyscan dye reagent was added. The tubes were incubated for 30 minutes at room temperature for four 5 second rounds of vortexing per sample. Each sample was then spun at 15000 rpm for 10 minutes and the resulting supernatant was removed. Each pellet was then resuspended in 1.0 mL of dissociation reagent from the Blysacan Assay kit. Duplicate 100 µl aliquots of the resulting solution were pipetted into two wells of a 96-well plate and read at an absorbance of 656 nm. Sample concentrations were calculated by comparing the sample absorbance to a standard curve as described in Example 5. Content of sGAG per gram was calculated by dividing sample sGAG content by total weight of sample. There was no significant difference in sGAG content in the base material. Furthermore, there was no significant reduction in sGAG by either NaOH or SDS/TBE. This suggests that neither SDS/TBE nor NaOH have an effect on the GAGs.

For fibronectin content, a total of 48 12 mm disk test samples were evaluated. Samples were weighed and weights recorded. Individual samples were placed in 1.5 mL eppendorf centrifuge tubes and 500 µl of sterile 10×PBS was added to each tube. Samples were pulverized with tissue grinders for 90 seconds per sample. Sample duplicates were tested by Bender MedSystems Humen Fibronectin ELISA kits as per manufacturer's instructions. Content of fibronectin per gram was calculated by dividing sample fibronectin content by total weight of sample. The quantity of fibronectin initially contained within the base material can be eliminated with the use of SDS/TBE as well as NaOH.

For hyaluronic acid testing, a total of 48 12 mm disk test samples were evaluated as described in Example 4. Content of hyaluronic acid was calculated by dividing the sample hyaluronic acid content by total weight of sample. There is no statistical difference between any of the groups tested. This is in keeping with the results of the sGAGs.

EXAMPLE 8

Visible Nuclei Content of Graft Material

Six lots of abdominal wall fascia (consisting of two tissue slabs each) were obtained and prepared similar to that described in Example 1. Briefly, the twelve tissue slabs were initially processed by mechanically removing a dense layer of adipose tissue. Subsequently, six sheets (one from each lot) were placed into 0.2% peracetic acid (PAA) for two hours on an orbital shaker. The remaining six sheets were treated in isopropyl alcohol (IPA) and acetone solutions before being further divided into two treatment groups. The first group was treated for one hour in 1 M NaOH at room temperature. The second group was placed into 0.1% sodium dodecyl sulfate (SDS) (37° C.) for one hour then 1×TBE (37° C.) for an additional hour (TBE=89 mM tris, borate, ethylene diamine tetraacetic acid solution). Both groups were rinsed four times in high purity water after treatment completion and disinfected in 0.2% PAA for two hours. After four rinses in high purity water, all tissue samples were stored at 4° C.

One 2 cm×2 cm sample was cut on the material for the testing procedure. A solution of Hoechst 33528 was made for staining the samples. A total of 90 mL of staining solution was made by diluting a stock solution of 1 mg/mL Hoechst in methanol to 1 μg/mL in phosphate buffered saline (90 μl of Hoechst stock into 90 mL of PBS). Each sample was incubated in 5 mL of Hoechst staining solution for 15 minutes at room temperature with shaking. After staining, each sample was rinsed 3 times with PBS for 5 minutes at room temperature with shaking. Stained samples were placed onto a glass microscope slide. A 22 mm×22 mm glass coverslip was placed on top of the sample and lightly pressed to remove any air bubbles. The slide with stained sample was then placed on the microscope stage. The stage was adjusted to put the sample underneath the objective at a random location for the sample. The focus was adjusted to provide an image with the most number of in focus nuclei as possible for that location. The image was then taken using the SpotRT software. The image was adjusted by selecting grayscale and negative to give the nuclear staining as dark dots on a light background. The brightness, contrast and gamma were adjusted to ensure the easiest determination of nuclei. Four images were taken at random locations on each sample. The images were printed onto sheets and the number of nuclei present was counted. If the image contained greater than 200 nuclei, the image was deemed too numerous to count. Once all of the counts were finished, the average and standard deviation for each lot was determined. The counts were displayed as number of nuclei per field.

The average nuclei count on the base material for a 20× field (measuring 0.263 mm$^2$) was deemed too numerous to count for the SDS/TBE processing in this Example. The process using NaOH effectively eliminated all visible nuclei.

EXAMPLE 9

Additional Biomechanical Testing

Additional subserous fascia ECM materials that had been chemically treated to remove lipids, disinfected, and then lyophilized, were tested for mechanical properties generally as described for Example 7 above. The results are set forth in Table 3 below, and compared to those of single layer porcine small intestinal submucosa (SIS) available from Cook Biotech Incorporated (West Lafayette, Ind.).

TABLE 3

Mechanical characteristics of processed porcine abdominal wall fascia and SIS.

|  | Abdominal Wall Fascia | | SIS | |
| --- | --- | --- | --- | --- |
|  | Average | Std. Dev | Average | Std. Dev |
| Tensile Strength at break (lbs) | 3.41 | 1.35 | 3.72 | 1.05 |
| Suture Strength (lbs) | 1.42 | 0.48 | 2.5 | 0.57 |
| Burst Strength (kPa) | 466 | 161 | 359 | 98 |
| Elongation At Break (%) | 71% | 15% | 33% | 5% |

As can be seen, the abdominal wall fascia ECM has good strength properties and is significantly more extensible than the SIS as evidenced by the elongation at break values.

EXAMPLE 10

Rat Abdominal Wall Testing

Additional subserous fascia ECM materials were prepared from porcine abdominal wall tissue sections according to Table 4 below. These materials were tested in a rat abdominal model.

TABLE 4

| Step | w/v ratio | Chemical/Solution | Time |
| --- | --- | --- | --- |
| 1 | 1:10 | IPA (99%) | 15 min |
| 2 | 1:10 | IPA | ½ hr |
| 3 | 1:10 | Acetone (pure) | ½ hr |
| 4 | 1:10 | IPA | 15 min |
| 5 | 1:10 | HPW (high purity water) | 5 min |
| 6 | 1:10 | HPW | 5 min |
| 7 | 1:10 | 1M NaOH | 1 hr |
| 8 | 1:10 | HPW | 5 min |
| 9 | 1:10 | HPW | 5 min |
| 10 | 1:10 | PAA Solution | 2 hr |
| 11 | 1:10 | HPW | 5 min |
| 12 | 1:10 | HPW | 5 min |
| 13 | 1:10 | HPW | 5 min |
| 14 | 1:10 | HPW | 5 min |

In addition to the fascia material above, a control sample was prepared using a 4-layer porcine small intestinal submucosa (SIS) material available from Cook Biotech Incorporated (West Lafayette, Ind.).

The fascia and SIS materials were used to prepare 2 cm×2 cm samples for use in repairing a 2 cm×2 cm defect created in a rat abdominal wall. A total of 60 rats were used. An abdominal skin and subcutaneous incision was made in each rat to expose the abdominal wall. A full-thickness abdominal/fascial wall defect measuring approximately 2 cm×2 cm was created in each rat abdomen. Either the fascia sample or the SIS sample was used to repair the defect. The implanted samples were evaluated at three different time points: 10 rats having SIS implants at 2 weeks, 8 rats having fascia implants at 2 weeks (2 rats died due to cecal adhesions), 10 rats having SIS implants at 4 weeks, 10 rats having fascia implants at 4 weeks, 10 rats having SIS at 8 weeks, and 10 rats having fascia implants at 8 weeks. At the time of explant, a dog-bone shaped test article was cut out of the center of each implanted sample. Test articles were mechanically tested to failure with the force at failure measured as the ultimate tensile force of the sample.

In general, the strength of the repair increased for both materials over time. In addition, there was no statistical difference between fascia and SIS at any time point. The ultimate tensile force data is summarized in Table 5 below. This data suggests that there is no difference in the repair strength over time between these two materials, and the strength of the materials increased over time for both samples.

TABLE 5

| | Ultimate Tensile Force (LBF) | | | | |
| --- | --- | --- | --- | --- | --- |
| | Abdominal Wall Fascia | | SIS 2.0 | | |
| | Average | Std. Dev. | Average | Std. Dev. | P-Value |
| 2 weeks | 0.75 | (0.61) | 0.89 | (0.35) | 0.66 |
| 4 weeks | 1.27 | (0.63) | 1.13 | (0.38) | 0.61 |
| 8 weeks | 1.73 | (0.68) | 1.71 | (1.14) | 0.97 |

After the samples were tested for Ultimate Tensile Force, a section of each remaining implanted sample was collected and fixed in formalin. The fixed samples were then embedded, sectioned, and stained with H&E. The histology supported the mechanical results in that there was little difference between the two materials in the cellular infiltration and remodeling at each time point. Some cellular ingrowth was shown in both samples at 2 weeks. At 4 weeks both materials exhibited more cellular infiltration and remodeling. At 8 weeks, both samples exhibited normal fibrovascular tissue with very little material remaining.

This Example shows that a graft material isolated from the abdominal wall of a porcine animal as described herein has similar strength over time as compared to a SIS material. Histology supported these findings with the abdominal wall fascia ECM material described herein showing similar remodeling characteristics as SIS.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. In addition, all publications cited herein are indicative of the abilities of those of ordinary skill in the art and are hereby incorporated by reference in their entirety as if individually incorporated by reference and fully set forth.

What is claimed is:

1. A bioresorbable collagenous and elastinous extracellular matrix graft material having high elasticity and strength, comprising an isolated, bioresorbable layer of highly extensible extracellular matrix material isolated from the abdominal wall of a porcine animal, said extracellular matrix material comprising collagen and elastin and comprising at least the subserous fascia from the abdominal wall, wherein the extracellular matrix material is essentially devoid of native cells, wherein the extracellular matrix material has a tensile strength at break of at least one pound and an elongation at break of at least about 50%, and wherein the extracellular matrix material has a lipid content of less than 15 percent by weight.

2. The graft material of claim 1, wherein said extracellular matrix material has a lipid content of less than 10 percent by weight.

3. The graft material of claim 1, wherein said layer also includes parietal peritoneum from the abdominal wall.

4. The graft material of claim 1, wherein said material is disinfected with an oxidizing disinfectant.

5. The graft material of claim 4, wherein said oxidizing disinfectant comprises a peroxy compound.

6. The graft material of claim 5, wherein said peroxy compound is a peracid.

7. The graft material of claim 6, wherein said peroxy compound is peracetic acid.

8. The graft material of claim 1, wherein said layer has a length of at least 20 cm and a width of at least 20 cm.

9. The graft material of claim 1 wherein said extracellular matrix material has a lipid content of less than 5 percent by weight.

10. The graft material of claim 1, comprising at least two said layers bonded to one another.

11. The graft material of claim 10, also comprising perforations that allow passage of fluid through the graft material.

12. The graft material of claim 10, wherein said layers are dehydrothermally bonded to one another.

13. The graft material of claim 1, in a dehydrated form and sealed in sterile condition within a package.

14. A bioresorbable collagenous and elastinous extracellular matrix graft material having high elasticity and strength, comprising an isolated, bioresorbable layer of highly extensible extracellular matrix material isolated from the abdominal wall of a porcine animal, said extracellular matrix material comprising collagen and elastin and comprising at least the subserous fascia from the abdominal wall, wherein the extracellular matrix material is essentially devoid of native cells, wherein the extracellular matrix material has a tensile strength at break of at least one pound and an elongation at break of at least about 50%, and wherein the extracellular matrix material is free from FGF-2.

15. The graft material of claim 14 wherein said extracellular matrix material comprises hyaluronic acid.

16. The graft material of claim 14 wherein said extracellular matrix material has a lipid content of less than 15 percent by weight.

17. The graft material of claim 14, comprising at least two said layers bonded to one another.

18. A bioresorbable collagenous and elastinous extracellular matrix graft material having high elasticity and strength, comprising two or more isolated, bioresorbable layers of highly extensible extracellular matrix material isolated from the abdominal wall of a porcine animal, wherein said layers are bonded to one another, said extracellular matrix material comprising collagen and elastin and comprising at least the subserous fascia from the abdominal wall, wherein the extracellular matrix material is essentially devoid of native cells, and wherein the extracellular matrix material has a tensile strength at break of at least one pound and an elongation at break of at least about 50%.

19. The graft material of claim 18 wherein said extracellular matrix material has a lipid content of less than 15 percent by weight.

20. The graft material of claim 18 wherein said extracellular matrix material has a lipid content of less than 10 percent by weight.

21. The graft material of claim 18, also comprising perforations that allow passage of fluid through the graft material.

22. The graft material of claim 18, wherein said layers are dehydrothermally bonded to one another.

23. The graft material of claim 18, wherein said layers also include parietal peritoneum from the abdominal wall.

24. The graft material of claim 18, in a dehydrated form and sealed in sterile condition within a package.

25. The graft material of claim 18, wherein said layers have a length of at least 20 cm and a width of at least 20 cm.

* * * * *